(12) United States Patent
Van de Bittner

(10) Patent No.: US 11,506,581 B2
(45) Date of Patent: Nov. 22, 2022

(54) MASS SPECTROMETRY COMPATIBLE SALT FORMATION FOR IONIC LIQUID SAMPLE PREPARATION

(71) Applicant: Agilent Technologies, Inc., Santa Clara, CA (US)

(72) Inventor: Genevieve Van de Bittner, Campbell, CA (US)

(73) Assignee: AGILENT TECHNOLOGIES, INC., Santa Clara, CA (US)

( * ) Notice: Subject to any disclaimer, the term of this patent is extended or adjusted under 35 U.S.C. 154(b) by 936 days.

(21) Appl. No.: 16/290,322

(22) Filed: Mar. 1, 2019

(65) Prior Publication Data

US 2019/0293530 A1    Sep. 26, 2019

Related U.S. Application Data

(60) Provisional application No. 62/723,873, filed on Aug. 28, 2018, provisional application No. 62/645,583, filed on Mar. 20, 2018.

(51) Int. Cl.
| | | |
|---|---|---|
| *G01N 1/40* | (2006.01) | |
| *B01D 11/04* | (2006.01) | |
| *B01D 15/38* | (2006.01) | |
| *G01N 30/72* | (2006.01) | |
| *G01N 33/68* | (2006.01) | |
| *G01N 1/30* | (2006.01) | |
| *G01N 1/34* | (2006.01) | |
| *G01N 30/06* | (2006.01) | |

(52) U.S. Cl.
CPC ......... *G01N 1/405* (2013.01); *B01D 11/0492* (2013.01); *B01D 15/3804* (2013.01); *G01N 1/30* (2013.01); *G01N 1/34* (2013.01); *G01N 30/7206* (2013.01); *G01N 30/7233* (2013.01); *G01N 33/6848* (2013.01); *G01N 2001/4061* (2013.01); *G01N 2001/4088* (2013.01); *G01N 2030/067* (2013.01); *G01N 2560/00* (2013.01)

(58) Field of Classification Search
None
See application file for complete search history.

(56) References Cited

U.S. PATENT DOCUMENTS

| | | | |
|---|---|---|---|
| 6,924,478 | B1 | 8/2005 | Zubarev et al. |
| 7,145,133 | B2 | 12/2006 | Thomson |
| 7,229,834 | B2 | 6/2007 | Chace |
| 7,507,953 | B2 | 3/2009 | Makarov et al. |
| 7,531,793 | B2 | 5/2009 | Satoh et al. |
| 7,534,996 | B2 | 5/2009 | Suits et al. |
| 2014/0273080 | A1 | 9/2014 | Apffel, Jr. |
| 2015/0369711 | A1 | 12/2015 | Smart et al. |

FOREIGN PATENT DOCUMENTS

WO    2003002622 A1    1/2003

*Primary Examiner* — Xiaoyun R Xu
(74) *Attorney, Agent, or Firm* — Mannava & Kang, P.C.

(57) ABSTRACT

Reagents and methods for obtaining a metabolite solution comprising a mass spectrometry compatible volatile salt or volatile compound.

20 Claims, 8 Drawing Sheets

PBS 1

PBS 2

BMIM OAc 10%

BMIM OAc 20%

BMIM OAc 30%

BMIM OAc 50%

MASS SPECTROMETRY COMPATIBLE SALT FORMATION FOR IONIC LIQUID SAMPLE PREPARATION

CROSS-REFERENCE TO RELATED APPLICATIONS

This application claims priority to the following two U.S. Provisional applications: U.S. Provisional Application Ser. No. 62/723,873 filed on Aug. 28, 2018 and U.S. Provisional Application Ser. No. 62/645,583 filed on Mar. 20, 2018, the entire disclosure of both Provisional Applications is incorporated herein by reference.

TECHNICAL FIELD

The present invention relates to the field of metabolomics, including methods, reagents, compositions, kits and systems for forming mass spectrometry compatible salts or compounds in a solution comprising metabolites. These methods may find applications in pharma and biopharma, clinical diagnostics, synthetic biology, environmental protection, food testing and agriculture, and forensic toxicology.

BACKGROUND

Metabolomics is a powerful tool which can be used in many areas, including to study diseases, disease progression, and the metabolic impact of newly developed therapeutics; measure disease biomarkers; optimize chemical production by measuring a metabolic flux; understand the impact of environment on organisms and detection of toxins; analyze food processing, quality and safety; and to detect drugs and their metabolites in a human sample. Strategies for using ionic liquids to lyse cells or other biological samples and quench metabolism during preparation of metabolomics samples have been developed, including as described in US Patent Publications US 2014/0273080 and US 2015/0369711, both incorporated herein by reference.

Ionic liquids are comprised of a positively charged organic ion (A) and a counterion (B). Prior to analysis of the metabolomic samples, the positively charged organic ion (A) is removed from the solution to prevent contamination of the liquid chromatography and mass spectrometry system and to prevent ion suppression of metabolites during mass spectrometry analysis. To remove the positively charged organic ion (A), a salt metathesis reaction is utilized. The components required for this reaction include: the ionic liquid used to lyse the cells or other biological sample and quench metabolism (AB) and an ionic compound (CD) that can interact with the ionic liquid to form a new ionic liquid (AD) that is itself a water-immiscible liquid or is miscible with a water-immiscible solvent or liquid.

During the salt metathesis reaction, the positively charged organic ion (A) moves from the aqueous phase to form an ionic complex (AD) that is itself a water-immiscible liquid or is miscible with a water-immiscible solvent or liquid. Ion (D) comes from the ionic compound (CD). Concurrently, ion (C) moves into the aqueous phase to take the place of the positively charged organic ion (A) and to form and ionic compound with counterion (B).

Ionic compound (CB) can have various properties, but it has been in some applications either an inorganic water-soluble salt, such as potassium chloride, or a water insoluble salt, such as silver phosphate. The drawback for forming an inorganic water-soluble salt is that these salts may cause ion suppression during mass spectrometry analysis and generally negatively impact the performance of mass spectrometry instruments. Water-insoluble salts offer some solution to this drawback. But forming a water-insoluble salt precipitate may require a further step of separating the salt precipitate from a metabolite solution. Depending on the identity of the water-insoluble salt, it may form insoluble precipitates with some metabolites, reducing the content of those metabolites in the metabolite-containing solution. Depending on the identity of the water-insoluble salt, an excess of counterions, such as phosphate, might remain in solution and may impact the LCMS analysis of the samples.

Thus, there is a need in the field for methods by which a salt metathesis reaction may be carried out such that species formed in the salt metathesis reaction are mass spectrometry-compatible.

SUMMARY

In one aspect, this disclosure provides methods for preparing an aqueous solution comprising metabolites and a mass-spectrometry compatible volatile salt or volatile compound, the methods comprise:
mixing
i) a fluorous compound comprising a cation that can form a volatile salt or volatile compound with
ii) a solution comprising metabolites and an ionic liquid comprising an anion that can form a volatile salt or volatile compound,
wherein the mixing is optionally in the presence of a fluorous solvent and/or other water-immiscible solvent or liquid, and
thereby obtaining a two-layer mixture in which a first layer is not miscible with a second layer, the second layer is an aqueous solution comprising metabolites and the volatile salt or volatile compound and the first layer is an water-immiscible phase comprising the positively charged organic ion of the ionic liquid; and
collecting the aqueous solution comprising metabolites and the volatile salt or volatile compound.

In the present methods, the anion may comprise one or more of the following: sulfate, bisulfate, carbonate, bicarbonate, acetate anion, formate anion, trifluoroacetate anion, a conjugate base of an organic acid with 1 to 15 carbons, sulfide, hydrogen sulfide, cyanide, dicyanamide, nitrate, trichloroacetate anion, hydroxide, borate, hydride or any mixture thereof.

In the present methods, the cation may comprise one or more of the following: ammonium, trimethyl ammonium, pyridinium ion, imidazolium ion, piperidinium ion, pyrimidine conjugate acid, hydrogen cation (hydron), hydronium, triethylammonium, diethylammonium, morpholinium, 4-methylmorpholinium, 1-methylpiperidinium, pyrrolidinium, a nitrogen-containing conjugate acid of a weak base, or any combination thereof.

In the present methods, the volatile salt or volatile compound may comprise:
one or more of the following anions: sulfate, bisulfate, carbonate, bicarbonate, acetate anion, formate anion, trifluoroacetate anion, a conjugate base of an organic acid with 1 to 15 carbons, sulfide, hydrogen sulfide, cyanide, dicyanamide, nitrate, trichloroacetate anion, hydroxide, borate, hydride or any combination thereof; and/or
one or more of the following cations: ammonium, trimethyl ammonium, pyridinium ion, imidazolium ion, piperidinium ion, pyrimidine conjugate acid, hydrogen cation (hydron), hydronium, triethylammonium, diethylammonium, morpholinium, 4-methylmorpholinium, 1-methylpiperidinium, pyrrolidinium, a nitrogen-containing conjugate acid of a weak base, or any combination thereof.

In some embodiments, the anion is one of the following anions: a heteroatom derivative, alkene derivative, alkyne derivative of an organic acid with 1 to 15 carbons. In some embodiments, the anion comprises acetate and/or the cation comprises ammonium cation ($NH_4^+$).

In some embodiments, the present methods are conducted in the presence of a water-immiscible solvent or liquid, such as for example, one or more of the following: hexane/hexanes, tetrahydrofuran, dichloromethane, chloroform, butane, cyclohexane, heptane/heptanes or any combination thereof.

In some embodiments, the volatile salt comprises ammonium acetate.

In some of the present methods, the volatile salt or volatile compound comprises one or more of the following compounds: formic acid, acetic acid, trifluoroacetic acid, ammonium formate, ammonium acetate, ammonium hydroxide, water, triethylamine acetate, triethylamine formate, diethylamine acetate, diethylamine formate, piperidine acetate, piperidine formate, ammonium bicarbonate, borate, hydride, 4-methylmorpholine, 1-methylpiperidine, pyrrolidine acetate, pyrrolidine formate, or any combination thereof.

In some of the present methods, the positively charged organic ion in the ionic liquid is defined by one of the following formulas (I) through (VI):

(I)

where each of $R^1$ and $R^2$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl;

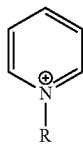
(II)

where R is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl;

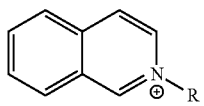
(III)

where R is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl;

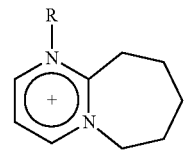
(IV)

where R is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl;

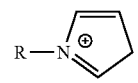
(V)

where R is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl;

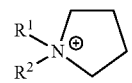
(VI)

where each of $R^1$ and $R^2$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl.

One or more of the positively charged organic ions may be 1-hexyl-3-methyl-imidazolium (HMIM) and/or 1-butyl-3-methyl-imidazolium (BMIM). In some of the methods, the ionic liquid comprises HMIM acetate, BMIM acetate, HMIM formate, and/or BMIM formate.

The present methods may be conducted with one or more of the fluorous compounds with the following general formula (VII):

$$[Z^1-(CH_2)_m-SO_2-N^{(-)}-SO_2-(CH_2)_p-Z^2].M^+ \quad (VII)$$

wherein: $M^+$ is the cation that can form a volatile salt or volatile compound and $Z^1$ and $Z^2$ are independently a perfluoroalkyl, an alkyl, a substituted alkyl, a perfluoroaryl, an aryl, or a substituted aryl, wherein $Z^1$ and $Z^2$ include together a combined total of 8 or more fluorinated (e.g., perfluorinated) carbon atoms (e.g., 9 or more, 10 or more, 11 or more, 12 or more, 13 or more, 14 or more, 15 or more, 16 or more, 17 or more, 18 or more, 19 or more, 20 or more, 30 or more or 40 or more fluorinated carbon atoms); and m and p are independently 0, 1 or 2.

The fluorous compound may comprise bis((perfluorohexyl)sulfonyl)imide formulated with one or more of the following cations: ammonium, trimethyl ammonium, pyridinium ion, imidazolium ion, piperidinium ion, pyrimidine conjugate acid, hydrogen cation (hydron), hydronium, triethylammonium, diethylammonium, morpholinium, 4-methylmorpholinium, 1-methylpiperidinium, pyrrolidinium or a nitrogen-containing conjugate acid of a weak base.

The fluorous compound may be ammonium bis((perfluorohexyl)sulfonyl)imide.

The fluorous solvent may comprise a perfluorocarbon (PFC) and/or a hydrofluoroether (HFE). The fluorous solvent may comprise perfluorohexane, perfluoromethylcyclohexane, perfluorodecalin, nanofluorobutyl methyl ether, or any combination thereof.

The solution comprising metabolites and the ionic liquid may also comprise one or more of water-miscible solvents. In some embodiments, the solution comprising metabolites and the ionic liquid also comprises acetonitrile, methanol, ethanol, acetone, dimethylformamide, dimethylsulfoxide, or any mixture thereof.

Further aspects of this disclosure include a method for manual or automatable ionic liquid workflow. The method may comprise the following three steps: 1) contacting a biological sample with one or more ionic liquids comprising one or more anions that can form a volatile salt or volatile compound, thereby obtaining a mixture comprising metabolites and the ionic liquid; 2) performing a metathesis reaction, and removing the cation of ionic liquid AB from the mixture comprising the metabolites by reacting the ionic liquid with a fluorous compound CD and producing a metabolite solution comprising a volatile salt or volatile compound; and 3) separating a water-immiscible phase from an aqueous phase, the aqueous phase comprising the metabolite solution. In this method, the metathesis reaction is performed as provided in this disclosure. The method may further comprise removing fluorine-containing contaminants from the metabolite solution, for example by, loading the metabolite solution onto a fluorous affinity resin, and thereby binding the fluorine-containing contaminants to the resin; and then eluting the solution comprising metabolites.

The biological sample in the method may comprise cells and contacting the biologic sample with the one or more ionic liquids may lyse the cells. The method further comprises separating cell and/or other debris comprising enzymes, proteins, DNA, RNA and/or lipids from the mixture comprising metabolites and the ionic liquid.

Further aspects of this disclosure include a kit for obtaining a metabolite solution, the kit comprising an ionic liquid that comprises an anion that can form a volatile salt or volatile compound and a fluorous compound comprising a cation that can form a volatile salt or volatile compound. The kit may further comprise one or more of the following: a phase separator material or column; a debris removal filtering device or column, a cell culture device that comprises a filter, a fluorous affinity column, a fluorous solvent, a water-immiscible liquid, a water-miscible solvent, a water-miscible solvent that is mixed with water, or any combination thereof. In some embodiments of the kit, at least one from the phase separator material or column; the debris removal filtering device or column, the cell culture device that comprises a filter, and/or the fluorous affinity column is in a multi-well format such as for example, a 96-well plate. In the kit, the ionic liquid may comprise a cation selected from 1-hexyl-3-methyl-imidazolium (HMIM) and 1-butyl-3-methyl-imidazolium (BMIM). In some of the kits, the ionic liquid comprises an acetate anion and wherein the fluorous compound comprises ammonium anion.

Some of the kits may comprise the fluorous compound which has the following formula (VII):

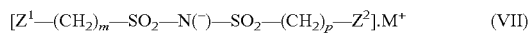

(VII)

wherein: M⁺ is a cation that can form a volatile salt or volatile compound;

$Z^1$ and $Z^2$ are independently a perfluoroalkyl, an alkyl, a substituted alkyl, a perfluoroaryl, an aryl, or a substituted aryl, wherein $Z^1$ and $Z^2$ include together a combined total of 8 or more fluorinated carbon atoms;

and m and p are independently 0, 1 or 2.

Further aspects include an analytical method for quantifying metabolites in a sample, the method comprising quenching enzymes in the sample with an ionic liquid comprising an anion that can form a volatile salt or volatile compound, generating a volatile salt or a volatile compound in a metathesis reaction of the ionic liquid with a fluorous compound comprising a cation that can form a volatile salt or volatile compound, and quantifying metabolites in the presence of the volatile salt or volatile compound by any of the following methods: direct injection mass spectrometry, liquid chromatography/mass spectrometry, gas chromatography/mass spectrometry, ion mobility/mass spectrometry, supercritical fluid chromatography/mass spectrometry, or any combination thereof. In the methods, a sample may comprise cells that have been lysed, by the ionic liquid or another method, before the enzymes are quenched.

BRIEF DESCRIPTION OF THE DRAWINGS

In FIG. 5A, metabolites were quantified in the presence (+) or absence (−) of 210 mM ammonium acetate. In FIG. 5B, metabolites were quantified in the presence (+) or absence (−) of 420 mM ammonium acetate.

DETAILED DESCRIPTION

Figure 1:
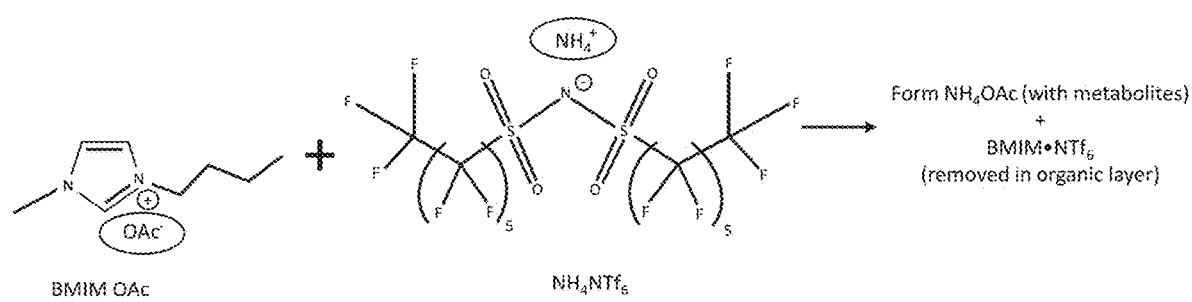
FIG. 1 is a schematic of a salt metathesis reaction producing mass spectrometry compatible ammonium acetate.

In one aspect, this disclosure provides a method in which a volatile, mass spectrometry-compatible salt or compound is formed during a metathesis reaction.

In this disclosure, the mass spectrometry-compatible volatile salt or volatile compound is defined as a salt or compound that readily evaporates into a gas under conditions existing within a mass spectrometer. In this disclosure, the term "volatile salt or volatile compound" is used interchangeably with the term "mass spectrometry-compatible volatile salt or volatile compound." While in general, not all volatile compounds known in the art may be mass-spectrometry compatible, it will be appreciated that in this disclosure volatile salts or volatile compounds include only those volatile salts or compounds that are mass spectrometry-compatible. Mass spectrometry-compatible means that these volatile salts or volatile compounds do not lead to significant ion suppression of metabolites and do not significantly degrade the sensitivity in the mass spectrometer system. The mass spectrometry-compatible volatile salt or compound does not significantly interfere with the performance of a mass spectrometer.

Suitable anions are anions that can form a volatile salt or volatile compound which is mass spectrometer-compatible. These anions are generally the anions (conjugate bases) of weak acids. Suitable cations are cations that can form a volatile salt or volatile compound. These cations are generally the cations (conjugate acids) of week bases. However, phosphate, monohydrogen phosphate, and dihydrogen phosphate do not form volatile salts although they are the conjugate bases of weak acids. Sulfate, bisulfate, and borate may be volatile, but their use is dependent on temperature used within the mass spectrometer source and how quickly they evaporate or convert into a chemical that can evaporate.

Methods in this disclosure include reacting in the metathesis reaction an ionic liquid, the ionic liquid comprising a positively charged organic ion (A) and an anion (B) that can form a volatile salt or volatile compound, with an ionic fluorous compound (CD) which comprises a cation (C) that can form a volatile salt or volatile compound.

In the methods, the metathesis reaction may be represented by the following scheme 1:

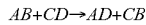
(Scheme 1)

Wherein:
A is a positively charged organic ion (A) in an ionic liquid,
B is an anion (B) that can form a volatile salt or volatile compound,
AB is an ionic liquid containing the anion (B)
C is a cation (C) that can form a volatile salt or volatile compound,
D is a fluorous compound,
CD is a fluorous compound comprising the cation (C),
AD is an ionic liquid miscible with a fluorous solvent and/or a solvent immiscible with water,
CB is a volatile salt or volatile compound.

These methods comprise mixing a mixture comprising metabolites, water and one or more ionic liquids comprising an anion that can form a volatile salt or volatile compound, with a fluorous compound comprising a cation that can form a volatile salt or volatile compound, in the presence of a fluorous solvent and/or other water immiscible solvent or liquid such as for example, hexane/hexanes, tetrahydrofuran, dichloromethane, chloroform, butane, cyclohexane, and heptane/heptanes or any combination thereof, and obtaining a two-phase composition comprising a first phase and a second phase, the second phase not miscible with the first phase. The first phase is a water-immiscible phase comprising a second, newly formed ionic liquid obtained by the metathesis reaction and the fluorous solvent and/or other water immiscible solvent or liquid, the second phase is a solution comprising metabolites and a volatile salt and/or volatile compound obtained by the metathesis reaction. The reaction mixture may further comprise one or more water-miscible solvent(s) and/or buffer and/or other additives. In some methods, the ionic liquid is 10 wt % to 100 wt % solution in water. The solution may further comprise at least one buffer and/or at least one water-miscible solvent. Preferably, the ionic liquid comprising anion B is a 50 wt % solution in water which may further comprise at least one water-miscible solvent and/or buffer and/or acids and/or bases and/or other additives.

These methods may be conducted at a temperature in the range from −80° C. to 300° C. Any temperature up to the boiling point of the solvent may be used.

In the present methods, the ionic liquid containing the anion is reacted with the fluorous compound containing the cation in molar ratios in the range from 1:100 to 100:1, respectively.

The volatile compounds or volatile salts obtained in the metathesis reaction of the present methods in this disclosure may comprise any of the following anions: sulfate, bisulfate, carbonate, bicarbonate, acetate anion, formate anion, trifluoroacetate anion, organic acids with approximately 15 or fewer carbons (including heteroatom derivatives, alkene derivatives, alkyne derivatives of organic acids), sulfide, hydrogen sulfide, cyanide, dicyanamide, nitrate, trichloroacetate anion, hydroxide, borate, hydride or any combination thereof.

The volatile compounds or volatile salts obtained in the metathesis reaction of the present methods in this disclosure may comprise any of the following cations: ammonium, trimethyl ammonium, pyridinium ion, imidazolium ion, piperidinium ion, pyrimidine conjugate acid, hydrogen cation (hydron), hydronium, triethylammonium, diethylammonium, morpholinium, 4-methylmorpholinium, 1-methylpiperidinium, pyrrolidinium, other nitrogen-containing conjugate acids of weak bases, or any combination thereof.

Some volatile compounds or volatile salts obtained in the metathesis reaction of the present methods comprise:
one or more of the following anions: sulfate, bisulfate, carbonate, bicarbonate, acetate anion, formate anion, trifluoroacetate anion, organic acids with approximately 15 or fewer carbons (including heteroatom derivatives, alkene derivatives, alkyne derivatives of organic acids), sulfide, hydrogen sulfide, cyanide, dicyanamide, nitrate, trichloroacetate anion, hydroxide, borate, hydride, or any combination thereof; and/or
one or more of the following cations: ammonium, trimethyl ammonium, pyridinium ion, imidazolium ion, piperidinium ion, pyrimidine conjugate acid, hydrogen cation (hydron), hydronium, triethylammonium, diethylammonium, morpholinium, 4-methylmorpholinium, 1-methylpiperidinium, pyrrolidinium, other nitrogen-containing conjugate acids of weak bases, or any combination thereof.

Particularly preferred volatile compounds or volatile salts obtained in the metathesis reaction of the present methods include, but are not limited to: formic acid, acetic acid, trifluoroacetic acid, ammonium formate, ammonium acetate, ammonium hydroxide, water, triethylamine acetate, triethylamine formate, diethylamine acetate, diethylamine formate, piperidine acetate, piperidine formate, ammonium bicarbonate, borate, hydride, 4-methylmorpholine, 1-methylpiperidine, pyrrolidine acetate, pyrrolidine formate, or any combination thereof.

A particularly preferred volatile, mass spectrometer-compatible salt or compound generated in the present methods is ammonium acetate.

In one aspect, the current disclosure provides a method which generates a volatile, mass spectrometer-compatible salt or compound mixed with a metabolite solution. The method may be practiced as a part of the metabolomics ionic liquid sample preparation workflow.

The present metathesis methods which generate a volatile, mass spectrometer-compatible salt or compound improve detection, analysis and separation of metabolites in a sample, including detection of metabolites by liquid chromatography mass spectrometry (LCMS) methods, gas chromatography mass spectrometry (GCMS) methods, ion mobility-mass spectrometry, and/or other mass spectrometry methods. Methods of the present disclosure may include analyzing metabolites by liquid chromatography-mass spectrometry systems. The analysis may include liquid chromatography, including a high-performance liquid chromatography, a micro- or nano-liquid chromatography or an ultra-high pressure liquid chromatography. The analysis may also include liquid chromatography/mass spectrometry (LCMS), ion mobility—mass spectrometry, gas chromatograph/mass spectrometry (GCMS), capillary electrophoresis (CE), capillary electrophoresis chromatography (CEC), or supercritical fluid chromatography-mass spectrometry.

The term "metabolites" is used herein in its conventional sense to refer to one or more compounds which are substrates or products of a metabolic process. Metabolites may include substrates or products which are produced by metabolic processes in a living cell including, but not limited to glycolysis, tricarboxylic acid cycle (i.e., TCA cycle, Krebs cycle), reductive pentose phosphate cycle (i.e., Calvin cycle), glycogen metabolism, pentose phosphate pathway, among other metabolic processes. Accordingly, metabolites may include, but are not limited to, glucose, glucose-6-phosphate, fructose-6-phosphate, fructose-1,6-phosphate, glyceraldehyde 3-phosphate, dihydroxyacetone phosphate, 1,3-bisphosphoglycerate, 3-phosphoglycerate, 2-phosphoglycerate, phosphoenolpyruvate, pyruvate, acetyl CoA, citrate, cis-aconitate, d-isocitrate, □-ketoglutarate, succinyl CoA, succinate, fumarate, malate, oxaloacetate, ribulose 1,5-bisphosphate, 3-phosphoglycerate, 1,3-bisphosphoglycerate, glyceraldehyde 3-phosphate, ribulose-5-phosphate, ethanol, acetaldehyde, pyruvic acid, 6-phosphogluconolactone, 6-phosphogluconate, ribose-5-phosphate, xylulose-5-phosphate, sedoheptulose 7-phosphate, erythrose 4-phosphate, among other metabolites. Metabolites may include drug compounds and drug metabolites or food compounds and food metabolites.

In the ionic liquid workflow of the present disclosure, an ionic liquid is added to a biological sample in order to lyse cells and/or denature and/or inhibit enzymes, and produce a mixture comprising metabolites. The ionic liquid comprises an anion that can form a volatile salt or volatile compound. By "lyse" cells, it is meant that the cells are ruptured or broken open such that the internal contents of the cells, including metabolites are released into the surrounding medium (i.e., ionic liquid which is usually a solution of an ionic liquid in water). In some embodiments, a cell lysis may further include a lysis of cellular organelles, for example the nucleus, mitochondria, ribosomes, chloroplasts, lysosomes, vacuoles, Golgi apparatus, centrioles, etc. such that the contents of the cellular organelles are also released into the surrounding medium.

The term "biological sample" refers to a whole organism or a subset of its tissues, cells and/or components (e.g. body fluids, including but not limited to blood, mucus, lymphatic fluid, synovial fluid, cerebrospinal fluid, saliva, amniotic fluid, amniotic cord blood, urine, vaginal fluid and semen). A "biological sample" can also refer to a homogenate, lysate or extract prepared from a whole organism or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, milk, blood cells, tumors, organs. In certain embodiments, the biologic sample has been removed from an animal, plant, and/or fungus.

Biological samples of the present disclosure may comprise cells. The term "cells" is used in its conventional sense to refer to the basic structural unit of a living eukaryotic and prokaryotic organism. In certain embodiments, cells include prokaryotic cells, such as bacteria. In other embodiments, cells include eukaryotic cells which may include, but are not limited to, tissue culture cell lines, yeast cells and primary cells which may be obtained from an animal, plant and/or fungus.

After the cell lysis/protein denaturation/enzyme disruption has been completed and proteins/cell debris are removed from the sample, further steps include the metathesis reaction by which the cation of the ionic liquid is separated from a metabolite solution and a volatile salt and/or compound is generated.

An ionic liquid is a salt in which counterions are poorly coordinated, and which results in the salts being in liquid form below 100° C. The term "ionic liquid" is used in its conventional sense to refer to a salt in liquid state. The ionic liquid may comprise water and other additives. For example, the ionic liquid may be a mixture with water. When mixed with water, the ratio of the ionic liquid to water may be in the range from 100:0 to 1:99 by weight. In this disclosure, an ionic liquid comprising water is referred to as an ionic liquid.

Suitable ionic liquids for the present methods comprise one or more anions that can form one or more volatile salt(s) or volatile compound(s).

In the present methods, the ionic liquid may comprise an anion that can form a volatile salt or volatile compound and a cation according to any of formulas (I)-(VI).

In some embodiments, the ionic liquid comprises a cation of Formula (I):

(I)

where each of $R^1$ and $R^2$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl.

In some embodiments, the ionic liquid comprises a cation of Formula (II):

(II)

where R is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl.

In some embodiments, the ionic liquid comprises a cation of Formula (III):

(III)

where R is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl.

In some embodiments, the ionic liquid comprises a cation of Formula (IV):

(IV)

where R is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl.

In some embodiments, the ionic liquid comprises a cation of Formula (V):

(V)

where R is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl.

In some embodiments, the ionic liquid comprises a cation of Formula (VI):

(VI)

where each of $R^1$ and $R^2$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl.

In some of the present methods, a mixture of at least two or more ionic liquids is used, wherein at least one ionic liquid in the mixture comprises one or more anions described in this disclosure.

Preferred ionic liquids include those comprising one or more of the following anions: sulfate, bisulfate, carbonate, bicarbonate, acetate anion, formate anion, trifluoroacetate anion, organic acids with approximately 15 or fewer carbons (including heteroatom derivatives, alkene derivatives, alkyne derivatives of organic acids), sulfide, hydrogen sulfide, cyanide, dicyanamide, nitrate, trichloroacetate anion, hydroxide, borate, hydride, or any combination thereof.

Preferred ionic liquids include those comprising one or more cations of any of Formulas (I) through (VI) and one or more of the following anions: sulfate, bisulfate, carbonate, bicarbonate, acetate anion, formate anion, trifluoroacetate anion, organic acids with approximately 15 or fewer carbons (including heteroatom derivatives, alkene derivatives, alkyne derivatives of organic acids), sulfide, hydrogen sulfide, cyanide, dicyanamide, nitrate, trichloroacetate anion, hydroxide, borate, hydride, or any combination thereof.

In some preferred embodiments, an ionic liquid comprises 1-hexyl-3-methyl-imidazolium (HMIM) and/or 1-butyl-3-methyl-imidazolium (BMIM) and one or more anions that can form a volatile salt or volatile compound.

In some preferred embodiments, an ionic liquid comprises HMIM and/or BMIM and one or more of the following anions: sulfate, bisulfate, carbonate, bicarbonate, acetate anion, formate anion, trifluoroacetate anion, organic acids with approximately 15 or fewer carbons (including heteroatom derivatives, alkene derivatives, alkyne derivatives of organic acids), sulfide, hydrogen sulfide, cyanide, dicyanamide, nitrate, trichloroacetate anion, hydroxide, borate, hydride, or any combination thereof.

Some methods in this disclosure are conducted with an ionic liquid comprising HMIM acetate and/or BMIM acetate, referred to in this disclosure as HMIM OAc and BMIM OAc, respectively.

The present metathesis methods are conducted with any of the ionic liquids described above and at least one fluorous compound with the following general formula (VII).

$$[Z^1\!-\!(CH_2)_m\!-\!SO_2\!-\!N(^-)\!-\!SO_2\!-\!(CH_2)_p\!-\!Z^2].M^+ \quad (VII)$$

wherein: $M^+$ is a cation that can form a volatile salt or volatile compound and preferably, $M^+$ is one or more of the following cations: ammonium, trimethyl ammonium, pyridinium ion, imidazolium ion, piperidinium ion, pyrimidine conjugate acid, hydrogen cation (hydron), hydronium, triethylammonium, diethylammonium, morpholinium, 4-methylmorpholinium, 1-methylpiperidinium, pyrrolidinium, other nitrogen-containing conjugate acids of weak bases, or any combination thereof; and $Z^1$ and $Z^2$ are independently a perfluoroalkyl, an alkyl, a substituted alkyl, a perfluoroaryl, an aryl, or a substituted aryl, wherein $Z^1$ and $Z^2$ include together a combined total of 8 or more fluorinated (e.g., perfluorinated) carbon atoms (e.g., 9 or more, 10 or more, 11 or more, 12 or more, 13 or more, 14 or more, 15 or more, 16 or more, 17 or more, 18 or more, 19 or more, 20 or more, 30 or more or 40 or more fluorinated carbon atoms); and m and p are independently 0, 1 or 2.

In certain embodiments of formula (VII), $Z^1$ and $Z^2$ are the same groups. In certain embodiments of formula (VII), $Z^1$ and $Z^2$ are different groups. In certain embodiments of formula (VII), $Z^1$ and $Z^2$ are each a fluorinated or perfluorinated group. In certain embodiments of formula (VII), at least one of $Z^1$ and $Z^2$ is a fluorinated or perfluorinated group. In certain embodiments of formula (VII), $Z^1$ and $Z^2$ are each a perfluoroalkyl. In certain embodiments of formula (VII), $Z^1$ and $Z^2$ are each perfluorobutyl. In certain embodiments of formula (VII), $Z^1$ and $Z^2$ are each perfluoropentyl. In certain embodiments of formula (VII), $Z^1$ and $Z^2$ are each perfluorohexyl. In certain embodiments of formula (VII), $Z^1$ and $Z^2$ are each a perfluoroheptyl. In certain embodiments of formula (VII), $Z^1$ and $Z^2$ are each a perfluorooctyl. In certain embodiments of formula (VII), $Z^1$ and $Z^2$ are each a perfluoroaryl. In certain embodiments of formula (IX), $Z^1$ and $Z^2$ include together a combined total of 10 or more perfluorinated carbon atoms. In certain embodiments of formula (VII), $Z^1$ and $Z^2$ include together a combined total of 12 or more perfluorinated carbon atoms.

In certain embodiments of formula (VII), m and p are each 0. In certain embodiments of formula (VII), m+p=1. In certain embodiments of formula (VII), m+p=2. In certain embodiments of formula (VII), m+p=3. In certain embodiments of formula (VII), m+p=4.

Preferred fluorous compounds in this disclosure include bis((perfluorohexyl)sulfonyl)imide (referred to as $NTf_6$ in this disclosure) formulated with a cation that can form a volatile salt or volatile compound. Preferred fluorous compounds in this disclosure include $NTf_6$ formulated with one or more of the following cations: ammonium, trimethyl ammonium, pyridinium ion, imidazolium ion, piperidinium ion, pyrimidine conjugate acid, hydrogen cation (hydron), hydronium, triethylammonium, diethylammonium, morpholinium, 4-methylmorpholinium, 1-methylpiperidinium, pyrrolidinium, other nitrogen-containing conjugate acids of weak bases, or any combination thereof.

A particularly preferred fluorous compound comprising a cation that can form a volatile salt or volatile compound is ammonium bis((perfluorohexyl)sulfonyl)imide ($NH_4$ $NTf_6$).

In methods of this disclosure, a cation counterion for the fluorous compound of formula (VII) and an anion counterion for an ionic liquid are selected such that: a volatile mass spectrometry compatible salt or compound is formed in the metathesis reaction. Accordingly, suitable ionic liquids and fluorous compounds include, but are not limited to: any ionic liquid comprising an anion and any fluorous compound comprising a cation that when reacted in the metathesis reaction generate any of the following salts/compounds: formic acid, acetic acid, trifluoroacetic acid, ammonium formate, ammonium acetate, ammonium hydroxide, water, triethylamine acetate, triethylamine formate, diethylamine acetate, diethylamine formate, piperidine acetate, piperidine formate, ammonium bicarbonate, borate, hydride, 4-methylmorpholine, 1-methylpiperidine, pyrrolidine acetate, pyrrolidine formate, or other volatile salt or compounds.

Referring to FIG. 1, it is a schematic of the metathesis reaction according to the present methods. A mixture comprising metabolites and BMIM OAc is reacted with $NH_4$ $NTf_6$. The mixture further comprises a fluorous solvent, water and, optionally, at least one water-miscible solvent. The reaction results in formation of a two-phase mixture, a first phase and a second phase, wherein the first phase is not miscible with the second phase, and wherein the first phase is an organic layer comprising the fluorous solvent and $BMIM.NTf_6$ and the second phase is a solution comprising metabolites and ammonium acetate.

Figure 2:
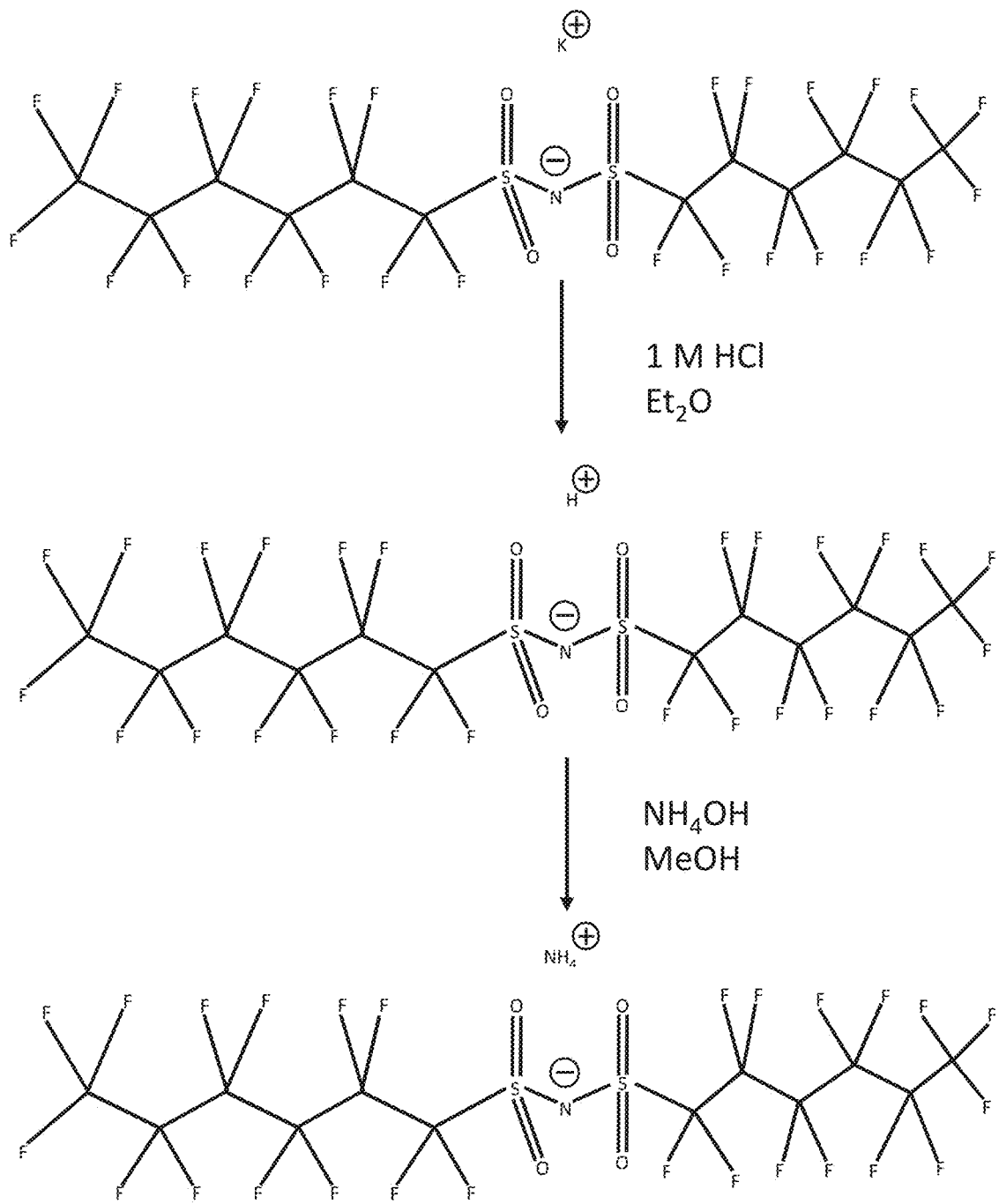
FIG. 2 is a schematic of synthesis of a fluorous compound comprising ammonium cation, using a method adapted from WO 2003/002622.

Referring to FIG. 2, it is a schematic of the synthesis of $NH_4$ $NTf_6$. The synthesis is conducted essentially as described in WO 2003/002622 A1. Specifically, in step 1, $NTf_6$ is obtained with a hydron cation, which is then reacted with ammonium hydroxide in the presence of methanol, as shown in FIG. 2. As is apparent to a person of skill, other fluorous compounds comprising a cation that can form a volatile salt or volatile compound may be obtained by following a protocol similar to the protocol described in connection with FIG. 2.

Metathesis methods of the present disclosure are conducted in the presence of a fluorous solvent which is not water-miscible and forms a separate water-immiscible phase in the metathesis reaction. A fluorous ionic liquid (AD) containing cation A from ionic liquid AB dissolves during the metathesis reaction into the water-immiscible phase and is thereby separated from a solution comprising metabolites. The metathesis reaction may also comprise a water-miscible solvent and/or other additives. Suitable water-miscible solvents include, but are not limited to acetonitrile, methanol, ethanol, acetone, dimethylformamide, dimethylsulfonamide and any mixture thereof. Other additives may include formic acid or acetic acid.

Suitable fluorous solvents include, but are not limited to, perfluorocarbons (PFCs) and hydrofluoroethers (HFEs). Perfluorocarbons include, but are not limited to, perfluorohexane, perfluoromethylcyclohexane and perfluorodecalin. Hydrofluoroethers include, but are not limited to, nanofluorobutyl methyl ether (e.g., HFE-7100). In some embodiments, the fluorous solvent is a hydrofluoroether, e.g. HFE-7100. The fluorous solvent may be neat or it may comprise additives. It will be appreciated that a fluorous solvent may be added before the metathesis reaction or after the metathesis reaction between an ionic liquid and a fluorous compound has been initiated, partially competed or fully completed. Alternatively, the fluorous solvent may be added simultaneously or soon after the mixing of a metabolite solution with ionic liquid comprising any of the anions of this disclosure with a fluorous compound comprising any of the cations of this disclosure.

The volatile salt or volatile compound that is formed in the metathesis reaction may be ammonium acetate and it can be formed during the salt metathesis step of the ionic liquid workflow. In other embodiments, other ammonium carboxylates or other volatile salts or compounds as described above, instead of or in addition to ammonium acetate, may be formed.

Previously, the ionic compound formed was a non-volatile inorganic salt (i.e. potassium chloride) that interfered with the detection of metabolites in the sample via LCMS, GCMS, or other metabolite analysis instruments/methods. Volatile ion pairs or volatile compounds do not interfere with the detection of metabolites in the sample via LCMS, GCMS, or other metabolite analysis instruments/methods to the same extent as inorganic ion pairs, since they are vaporized at temperatures commonly used during the mass spectrometry analysis.

This disclosure provides methods in which a volatile ion pair or volatile compound is formed, such as for example ammonium acetate, during the ionic liquid metabolomics sample preparation method. Formation of this volatile ion pair or volatile compound, such as for example, ammonium acetate, leads to an improved metabolite peak shape, metabolite resolution, and sensitivity to metabolite ions when analyzed by LCMS in particular, or by other metabolite detection methods. The ammonium acetate is also expected to have fewer long-term impacts than water soluble inorganic salts on the sensitivity and performance of LCMS systems that are used to analyze metabolomic samples prepared using the ionic liquid method. The ammonium acetate is also expected to have fewer long-term impacts than cation A of ionic liquid AB on the sensitivity and performance of LCMS systems that are used to analyze metabolomic samples prepared using the ionic liquid method.

Further methods of the present disclosure include a method of obtaining a metabolite solution, comprising a step of lysing a biological sample. These embodiments comprise lysing a biological sample with an ionic liquid comprising one or more anions provided in this disclosure, separating a solution comprising metabolites and the ionic liquid from lysis debris, and performing the metathesis reaction with a fluorous compound comprising one or more cations that can form a volatile salt or volatile compound provided in this disclosure. Any of the ionic liquids described in this disclosure can be used either alone or in combination with other ionic liquids.

The present disclosure provides a lysis solution comprising from 5 wt % to 100 wt % of an ionic liquid comprising one or more anions described in this disclosure. The lysis solution is typically water-based. It may further comprise one or more of water-miscible solvents, colorants, pH indicators, acids, bases, and/or buffers. The lysis reaction may be conducted at room temperature. The duration of the lysis reaction may vary from simply mixing the biological sample with the lysis solution to mixing and incubating the mixture for a period of time. Typically, the volume of the lysis solution depends on the volume/weight of a biological sample. Typically, from 10 to 2000 volumes of the lysis solution may be used per one volume or weight equivalent of a biological sample. For example, from 5 µl to 1,000 µl of the lysis solution may be used for 0.5 µl of a biological sample.

After the lysis of the biological sample has been completed, a step of separating the solution comprising the metabolites and the ionic liquid from unwanted debris may be conducted as needed, depending on the biological sample. The debris may include, depending on a biological sample, cell membranes, fat, denatured proteins, DNA, RNA etc. The step of separating the debris may include, but is not limited to, centrifugation, filtration and/or column chromatography. Other methods, known to a person of skill for separating solids from a solution may be used as well.

Figure 3A:
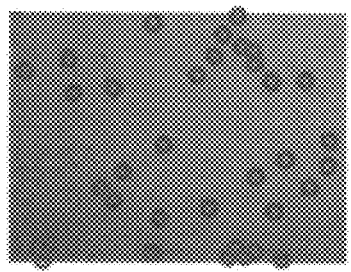
FIGS. 3A-3F depict cell lysis of leukemia cells. Panels 3A and 3B are controls with PBS showing unaffected cells. Panels 3C through 3F showing lysis of the cells with BMIM OAc in concentrations 10%, 20%, 30% or 50%, respectively.
Figure 3B:
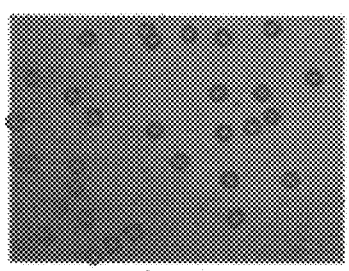
Figure 3C:
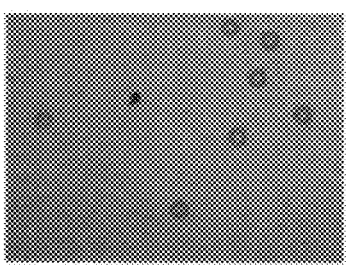
Figure 3D:
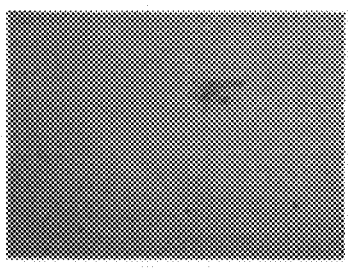
Figure 3E:
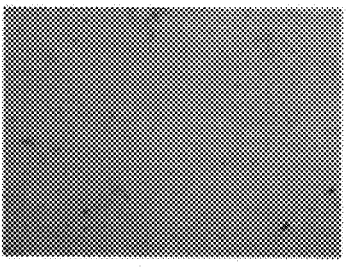
Figure 3F:
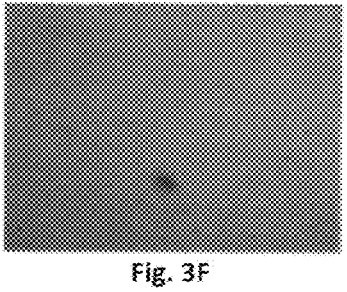

Referring to FIGS. 3A-3F, these are pictures of cells lysed with a cell lysis buffer comprising various concentrations of an ionic liquid comprising acetate (10, 20, 30, or 50% BMIM OAc in water (w/v)). FIGS. 3A and 3B depict control cells suspended in PBS. The controls show no significant cell lysis. FIGS. 3C through 3F show that the ionic liquid (BMIM OAc in various concentrations in water (w/v) as denoted in FIGS. 3C through 3F) lyses cells efficiently, and the efficiency of the reaction depends of the concentration of BMIM OAc, and/or the amount of BMIM OAc, and/or the amount of cells/size of the biological sample. All or nearly all cells are lysed with a water-based lysis solution comprising 50 wt % BMIM OAc as shown in FIG. 3F, while some intact cells are still present when a water-based lysis solution comprising 10 wt % BMIM OAc is used, as shown in FIG. 3C.

Figure 4:
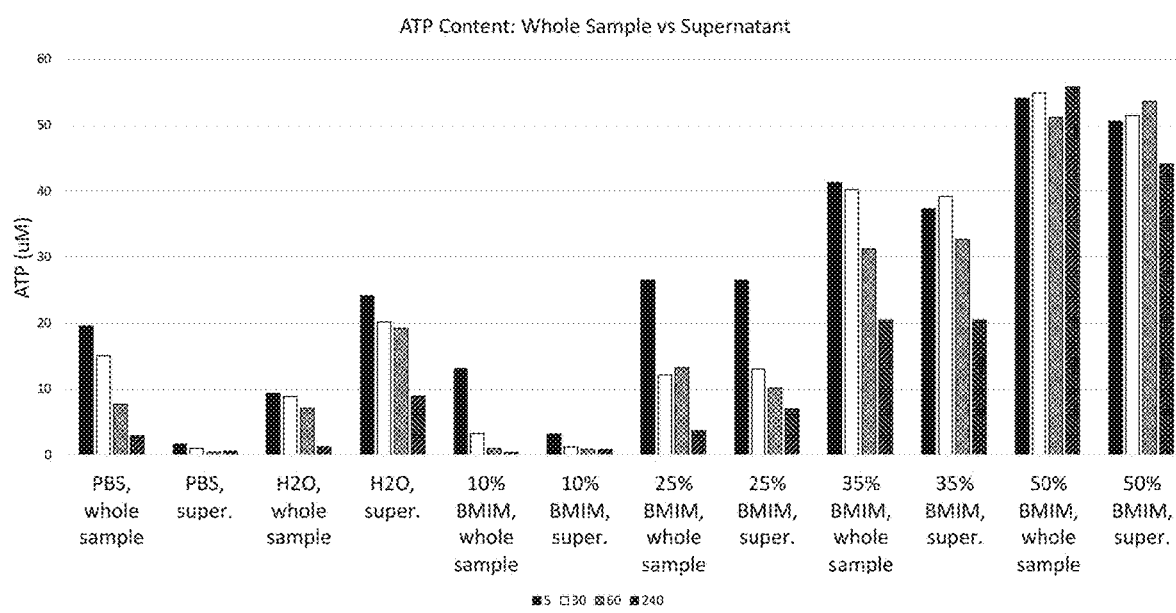
FIG. 4 reports results of quenching ATP metabolism with 50% BMIM acetate.

Referring to FIG. 4, it reports results of an enzymatic reaction which measures the amount of ATP in a cell lysate. As shown in FIG. 4, an ionic liquid comprising the acetate anion quenched efficiently enzymes in a cell lysate and thereby prevented ATP degradation in the cell lysate. The effect was time dependent—the amount of intact ATP was decreased as the function of time after cell harvest. However, the ionic liquid comprising the acetate anion prevented degradation of ATP. The effect was concentration-dependent. A lysis solution comprising 50% of BMIM OAc in water (w/v) quenched the ATP metabolism more efficiently than a lysis solution comprising 10% of BMIM OAc in water (w/v).

Further aspects of this disclosure provide methods for analyzing a sample comprising metabolites and one or more volatile salt(s) or compound(s). These analytic methods may be used in various industries, including in pharma and biopharma, clinical diagnostics, academia, synthetic biology, environmental protection, food testing and agriculture, and forensic toxicology. The analytic methods may be conducted in order to study the metabolic impact of newly developed therapeutics; measure disease biomarkers; optimize chemical production by measuring a metabolic flux; understand the impact of environment on organisms and detection of toxins; analyze food processing, quality and safety; or to detect drugs and their metabolites in a human sample.

The analytic methods include, but are not limited to, analyzing metabolites by liquid chromatography and/or mass spectrometry systems. The analysis may include liquid chromatography (LC), including a high-performance liquid chromatography (HPLC), a micro- or nano-liquid chromatography or an ultra-high pressure liquid chromatography (UHPLC). The analysis may also include liquid chromatography/mass spectrometry (LCMS), ion mobility-mass spectrometry, gas chromatograph/mass spectrometry (GCMS), capillary electrophoresis (CE), capillary electrophoresis chromatography (CEC), and/or supercritical fluid chromatography-mass spectrometry.

An analysis of a sample comprising metabolites and a volatile salt and/or volatile compound may be conducted by using any convenient protocol, such as for example, by mass spectrometry, infrared spectroscopy, UV-vis spectroscopy, colorimetry and nuclear magnetic resonance spectroscopy. In certain embodiments, a chemical analysis is conducted by gas chromatography-mass spectrometry. In other embodiments, a chemical analysis is conducted by liquid chromatography-mass spectrometry, ion mobility mass spectrometry, and/or supercritical fluid chromatography-mass spectrometry.

Methods of the present disclosure may include analyzing metabolites by liquid chromatography and mass spectrometry systems. The analysis may include liquid chromatography, including a high-performance liquid chromatography, a micro- or nano-liquid chromatography or an ultra-high pressure liquid chromatography. The analysis may also include liquid chromatography/mass spectrometry (LCMS), ion mobility-mass spectrometry, gas chromatograph/mass spectrometry (GCMS), capillary electrophoresis (CE), capillary electrophoresis chromatography (CEC), and/or supercritical fluid chromatography-mass spectrometry.

Mass spectrometer systems for use in the subject methods may be any convenient mass spectrometry system, which in general contains an ion source for ionizing a sample, a mass analyzer for separating ions, and a detector that detects the ions. In certain cases, the mass spectrometer may be a so-called "tandem" mass spectrometer that is capable of isolating precursor ions, fragmenting the precursor ions, and analyzing the fragmented precursor ions. Such systems are well known in the art (see, e.g., U.S. Pat. Nos. 7,534,996, 7,531,793, 7,507,953, 7,145,133, 7,229,834 and 6,924,478) and may be implemented in a variety of configurations. In certain embodiments, tandem mass spectrometry may be done using individual mass analyzers that are separated in space or, in certain cases, using a single mass spectrometer in which the different selection steps are separated in time. Tandem MS "in space" involves the physical separation of the instrument components (QqQ or QTOF) whereas a tandem MS "in time" involves the use of an ion trap.

An example mass spectrometer system may contain an ion source containing an ionization device, a mass analyzer and a detector. As is conventional in the art, the ion source and the mass analyzer are separated by one or more intermediate vacuum chambers into which ions are transferred from the ion source via, e.g., a transfer capillary or the like. Also as is conventional in the art, the intermediate vacuum chamber may also contain a skimmer to enrich analyte ions (relative to solvent ions and gas) contained in the ion beam exiting the transfer capillary prior to its entry into the ion transfer optics (e.g., an ion guide, or the like) leading to a mass analyzer in high vacuum.

The ion source may rely on any type of ionization method, including but not limited to electrospray ionization (ESI), atmospheric pressure chemical ionization (APCI), electron impact (EI), atmospheric pressure photoionization (APPI), matrix-assisted laser desorption ionization (MALDI) or inductively coupled plasma (ICP) ionization, for example, or any combination thereof (to provide a so-called "multi-mode" ionization source). In one embodiment, the precursor ions may be made by EI, ESI or MALDI, and a selected precursor ion may be fragmented by collision or using photons to produce product ions that are subsequently analyzed. Likewise, any of a variety of different mass analyzers may be employed, including time of flight (TOF), Fourier transform ion cyclotron resonance (FTICR), ion trap, quadrupole or double focusing magnetic electric sector mass analyzers, or any hybrid thereof. In one embodiment, the mass analyzer may be a sector, transmission quadrupole, or time-of-flight mass analyzer.

Figure 5A:
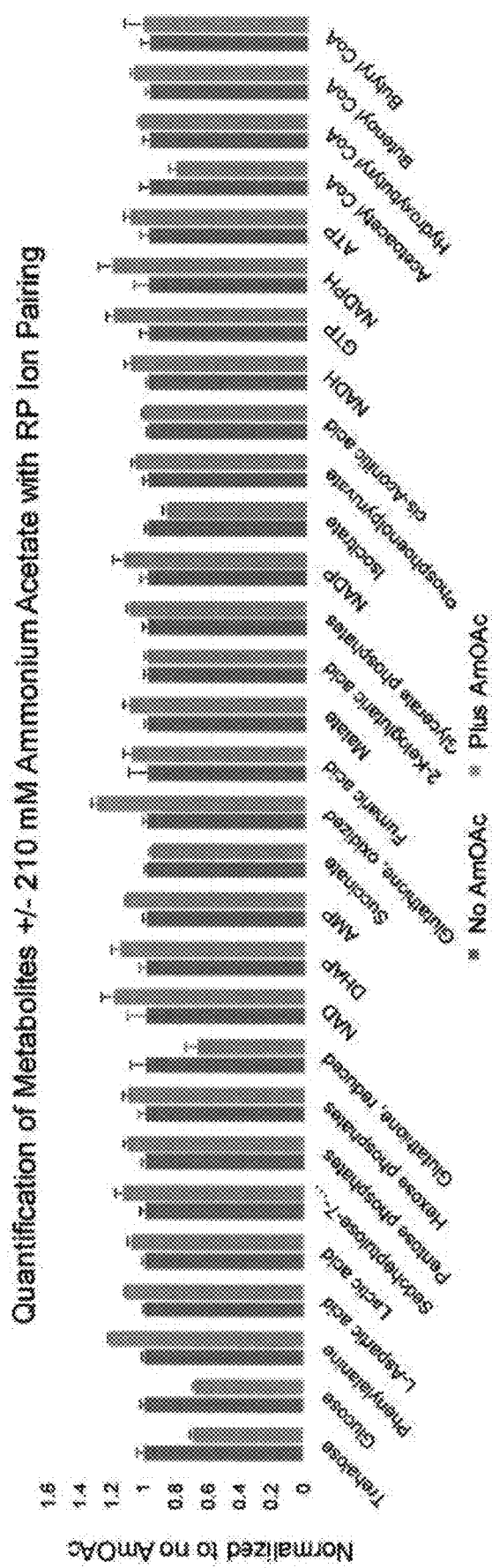
FIGS. 5A-5B report mass-spectrometry results of a metabolite sample analysis comprising ammonium acetate.
Figure 5B:
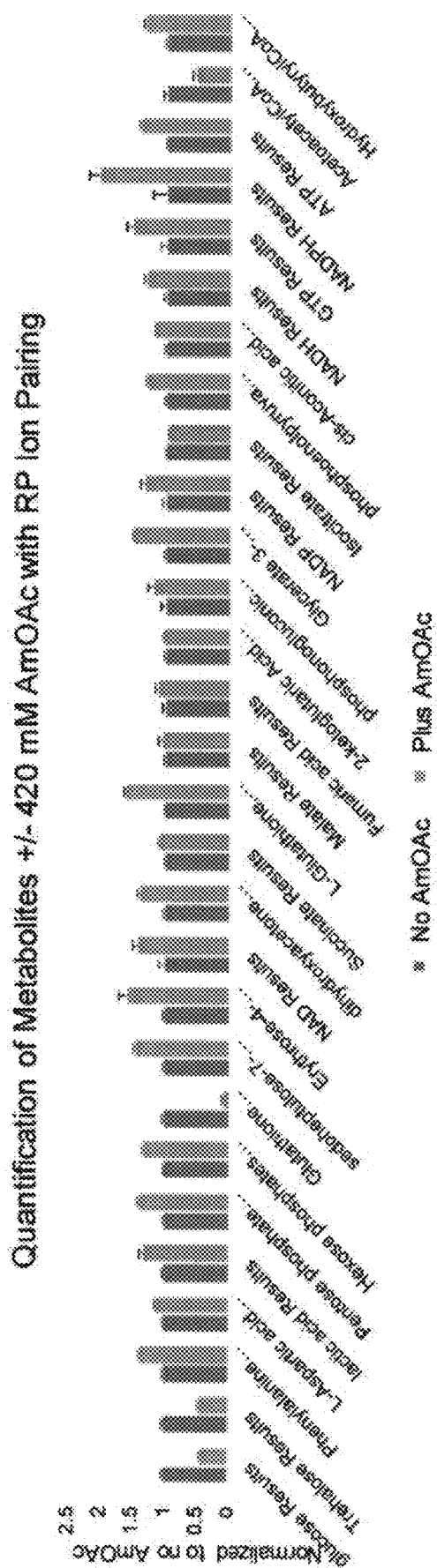

Referring to FIGS. 5A and 5B, they report results of a liquid chromatography/mass spectrometry analysis for various metabolites in the presence or absence of a volatile salt (ammonium acetate, AmOAc). Ion counts for various metabolites was measured in the presence of 210 mM ammonium acetate (FIG. 5A) or 420 mM ammonium acetate (FIG. 5B). The measurements were compared to metabolite standards without ammonium acetate. As can be seen from FIGS. 5A and 5B, for many metabolite standards, the peak areas are either equivalent to or greater than the peak areas without added ammonium acetate.

Figure 6:
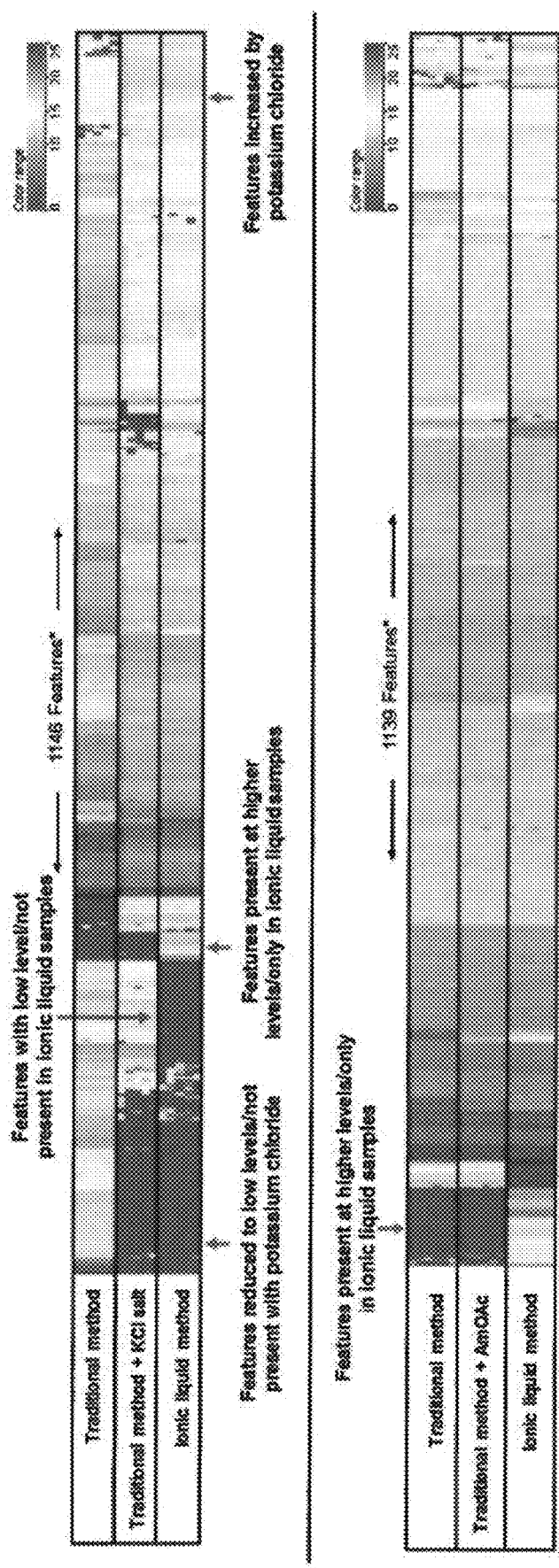
FIG. 6 are spectra of relative peak areas of compounds detected in lysed cell samples prepared using either an ionic liquid workflow which forms potassium chloride (the upper panel)) or an ionic liquid workflow which forms ammonium acetate (the lower panel).

Referring to FIG. 6, it reports results of a comparative analysis in which metabolites were quantified after being obtained either by the traditional metabolomic sample preparation method (the upper panels), by the traditional metabolomic sample preparation method with potassium chloride or ammonium acetate added to the samples (the middle panels) or by the ionic liquid workflow that forms potassium chloride or ammonium acetate (the lower panels).

Several different approaches have been attempted to remove unwanted inorganic salts from an aqueous sample of metabolites that are created during the ionic liquid workflow. Most of these approaches have not successfully removed the salt(s) without significantly impacting the metabolite sample and/or the detection of the metabolites of interest in the metabolite sample. Previous approaches include evaporation and re-dissolution of the metabolites in an organic solvent (major loss of nearly all classes of polar metabolites), salt precipitation through formation of a relatively insoluble silver chloride salt (loss of phosphate containing metabolites), magnetic ionic liquids, and a combination of SEC, ion exchange, and PGC types of chromatography. Another recently described approach was to form the water insoluble silver phosphate salt in the presence of excess phosphate containing compounds to prevent the precipitation of phosphate-containing metabolites.

The main advantages of formation of volatile salt or volatile compound, i.e. ammonium acetate, instead of an insoluble salt are 1) excess phosphate-containing compounds are not needed to prevent the precipitation of phosphate containing metabolites, and 2) there is no formation of a solid precipitate, which may interfere with liquid handling steps for some metabolomics sample preparation workflows.

Some embodiments of the present disclosure include using 1-butyl-3-methyl-imidazolium (BMIM) acetate as the ionic liquid (AB) that is used to lyse cells and/or quench metabolism. Other ionic liquids containing acetate or other carboxylate anions are suitable as well.

In some embodiments of the present disclosure, a fluorous compound comprises ammonium as a cation. One preferred fluorous compound (CD) used during the salt metathesis reaction is ammonium $NTf_6$, which is the ammonium salt of the fluorous $NTf_6$ compound.

Further aspects of this disclosure provide a method for manual or automatable ionic liquid workflow. This method comprises: 1) contacting a biological sample with one or more ionic liquids comprising one or more anions that can form a volatile salt or volatile compound, thereby obtaining a mixture comprising metabolites and the ionic liquid; 2) performing a metathesis reaction, and removing the cation of ionic liquid AB from the mixture comprising the metabolites by reacting the ionic liquid with a fluorous compound CD and producing a metabolite solution comprising a volatile salt or volatile compound; and 3) separating a water-immiscible phase from an aqueous phase, the aqueous phase comprising the metabolite solution In this method, the metathesis reaction may be performed as provided in this disclosure.

Further embodiments of the method for manual or automatable ionic liquid workflow may comprise a step of removing fluorine-containing contaminants from the metabolite solution. The fluorine-containing contaminants may include hydrolyzed by-products of the compound of the formula (VII). Examples of the fluorine-containing contaminants include, but are not limited to, a fluorous sulfonate and/or a fluorous sulfonamide. In some embodiments, the fluorine-containing contaminants are removed from the metabolite solution by loading the metabolite solution onto a fluorous affinity resin, and thereby binding the fluorine-containing contaminants to the resin; and eluting the solution comprising metabolites.

The method for manual or automatable ionic liquid workflow may be performed with any of biological samples described in this disclosure. Some of the biological samples may comprise cells and contacting such biologic samples with the one or more ionic liquids may lyse the cells.

Some of the embodiments of the method for manual or automatable ionic liquid workflow may further comprise separating cell and/or other debris comprising enzymes, proteins, DNA, RNA and/or lipids from the mixture comprising metabolites and the ionic liquid.

Further aspects of this disclosure include a kit for obtaining a metabolite solution, the kit comprising an ionic liquid that comprises an anion that can form a volatile salt or volatile compound and a fluorous compound comprising a cation that can form a volatile salt or volatile compound. The kit may further comprise one or more of the following: a phase separator material or column; a debris removal filtering device or column, a cell culture device that comprises a filter, a fluorous affinity column, a fluorous solvent, a water-immiscible solvent or liquid, a water-miscible solvent, a water-miscible solvent that is mixed with water, or any combination thereof. In the kit, at least one from the phase separator material or column; the debris removal filtering device or column, the cell culture device that comprises a filter, and/or the fluorous affinity column is in a multi-well format, such as for example, a 96-well plate.

In the kits, the ionic liquid may comprise a cation selected from 1-hexyl-3-methyl-imidazolium (HMIM) and 1-butyl-3-methyl-imidazolium (BMIM). Some of the kits comprise the ionic liquid comprises an acetate anion and wherein the fluorous compound comprises ammonium anion. In some of the kits, the fluorous compound is the compound of the formula (VII).

Figure 7:
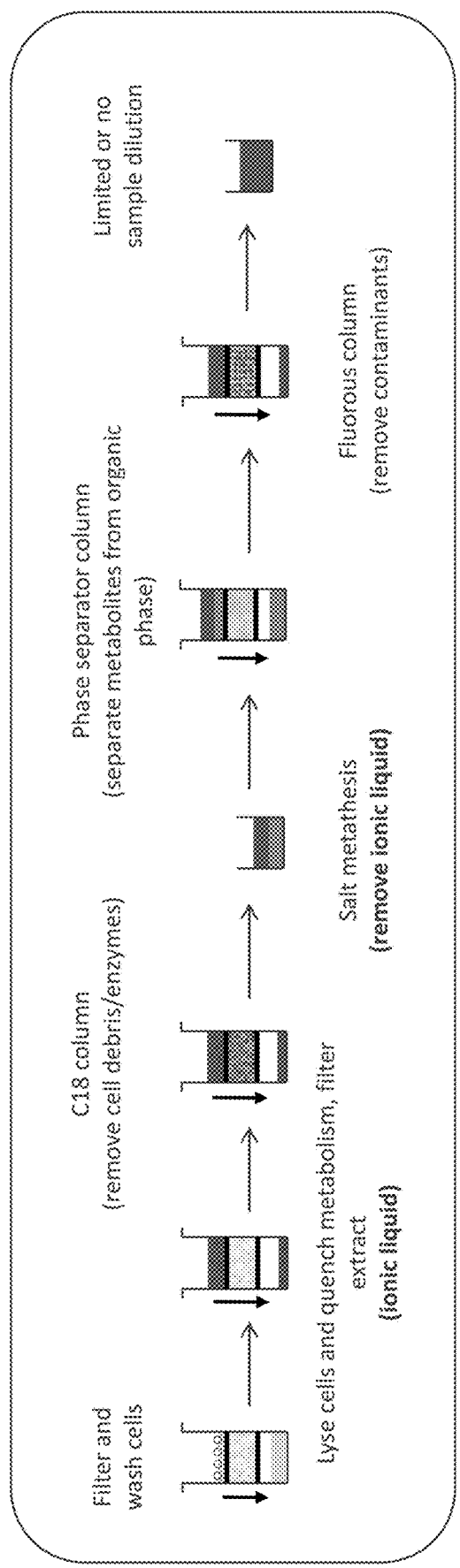
FIG. 7 is a diagram of the manual or automatable ionic liquid workflow.

FIG. 7 is a diagram of the manual or automatable ionic liquid workflow. FIG. 7 diagrams steps of lysing cells, removing cell debris and enzymes, performing the metathesis reaction, separating the water-immiscible phase, and removing fluorous contaminants. As can be seen in FIG. 7, cells or other biological sample may be lysed or contacted with an ionic liquid comprising an anion that can form a volatile salt or volatile compound. After the lysis, cell debris/enzymes can be removed by passing a lysate through a SPE chromatography column. For example, a C18 SPE plate may be used in order to process a number of microsamples simultaneously. The sample can also be "cleaned-up" using other SPE columns, molecular weight cutoff filters, and/or centrifugation.

The separation of a solution comprising metabolites from the water-immiscible phase comprising a complex of an ionic liquid with a fluorous compound (AD) can be performed in a phase separator plate.

Finally, the metabolite solution can be further passed through a fluorous affinity resin in order to remove fluorine-containing contaminants. For example, si-fluorochrom plates can be used.

Any conventional fluorous affinity resins may be utilized in the methods. Suitable fluorous affinity resins include, but are not limited to, fluorous affinity chromatography resins such as Fluoro-Pak™ and Fluoro-Pak™ II columns (Berry & Associates) and SiliaBond™ Fluorochrom (SiliCycle). Suitable fluorous affinity resins include a fluorous silica which comprises silicon dioxide derivatized with fluorous carbon chains. Suitable fluorous affinity resins also include fluorous styrene-based, benzyl-based and/or divinyl-benzyl-based polymers.

Suitable elution solvents include methanol, ethanol, isopropanol, acetone, acetonitrile, tetrahydrofuran, and any combination thereof. Any of the elution solvents may be used either neat or as a mixture with water in a ratio selected from the range from 100:0 to 0:100 by weight of the solvent to water.

Preferably, the solvent is used as a 0.1% to 99% solution in water.

At least in some embodiments, the elution solvent may comprise an additive. Suitable additives may include a protonation reagent. In some embodiments, the additive is a carboxylic acid. In some embodiments, the additive is formic acid. In some embodiments, the additive is acetic acid. In some embodiments, the elution solvent comprises acetonitrile and optionally a carboxylic acid which may be formic acid. In some embodiments, the elution solvent is a 0.1% to 80% solution of acetonitrile in water which further optionally comprises from 0.01% to 5% of formic acid.

Further aspects of this disclosure provide an analytical method for quantifying metabolites in a sample, the method comprising quenching enzymes in the sample with an ionic liquid comprising an anion that can form a volatile salt or volatile compound, generating a volatile salt or volatile compound in a metathesis reaction of the ionic liquid with a fluorous compound comprising a cation that can form a volatile salt or volatile compound, and quantifying metabolites in the presence of the volatile salt or volatile compound by any of the following methods: direct injection mass spectrometry, liquid chromatography/mass spectrometry, gas chromatography/mass spectrometry, ion mobility/mass spectrometry, supercritical fluid chromatography/mass spectrometry, or any combination thereof. In these methods, the sample may comprise cells that have been lysed before the enzymes are quenched.

This disclosure also provides the following non-limiting examples.

Example 1. Preparation of a Metabolomics Sample

Cells are filtered and washed with PBS/DPBS or isotonic NaCl (temperature can vary from 0.5° C. to 37° C.). Cells are lysed and metabolism is quenched with BMIM acetate, and the cell lysate is passed through a filter. A volume of water (±buffer or acid or base) is added to clear the hold-up volume of the plate. This water may be added prior to pulling the cell lysate through the filter to reduce the viscosity of the cell lysate solution and make it easier to pull the cell lysate solution through the filter plate. The filtered lysate solution comprises metabolites and the ionic liquid.

This metabolite solution is "cleaned-up" on a C18 SPE column and an elution solvent (i.e. mobile phase) is used to push the polar metabolites off the column. The sample can also be "cleaned-up" using other SPE columns, or molecular weight cutoff filters, and/or centrifugation.

BMIM is removed from the metabolite solution through a salt metathesis reaction with $NH_4$-$NTf_6$ in the presence of a fluorous liquid, i.e. HFE 7100. BMIM goes into the water-immiscible layer to form a salt with the $NTf_6$, and the ammonium ion transfers to the aqueous layer and forms a volatile salt with the acetate originally associated with BMIM.

The volatile ammonium acetate salt is mass spectrometry compatible, has limited impact on metabolite peak shapes, and has limited ion suppression effects on metabolites. Furthermore, the ammonium acetate does not significantly build up in the mass spectrometry system over time as it vaporizes at the temperatures and pressures used for mass spectrometry analysis.

Any hydrolyzed $NTf_6$ formed is removed using fluorous SPE columns.

For injection of metabolite samples onto a liquid chromatography column, the samples may be diluted in water and/or a water-miscible solvent, such as acetonitrile, methanol, ethanol, isopropanol, acetone or other water miscible solvent to reduce the ammonium acetate concentration. To account for sample dilution, larger sample volumes of the diluted solution might be injected.

Example 2. Lysis of K562 Leukemia Cells with BMIM Acetate

BMIM acetate solutions in water (w/v) were made at the indicated percentages (10, 20, 30 and 50%). 50 µl of the specified BMIM acetate solution was added to 500,000 K562 cells that had been washed with PBS and pelleted. The BMIM cell solutions were vortexed for approximately 1 min. 1 µl of each BMIM acetate cell solution was added to 19 µl PBS, and this solution was diluted 1:1 with trypan blue to label cells with lysed membranes. As a control, 1 ml of PBS was added to ~500,000 K562 cells washed with PBS. 20 µl of the control solution was diluted 1:1 with trypan blue to label any cells with lysed membranes. All cell samples were imaged using a Countess imager (Invitrogen). These pictures are shown as FIG. 3A through FIG. 3F.

Cells not stained by trypan blue (non-lysed cells) are circled. See controls in FIGS. 3A and 3B. 10% BMIM OAc does not lead to complete cell lysis (intact cells are seen), as shown in FIG. 3C. In contrast, 20, 30 and 50% BMIM OAc solutions appear to lyse all cells. See FIGS. 3D through 3F, respectively. 20 and 30% BMIM OAc solutions contain more lysed cells that have a circular shape that are trypan blue stained than the 50% BMIM OAc solution, suggesting that the cells/cell membranes are more completely disrupted with the 50% BMIM OAc solution.

Example 3. Analysis of K562 Leukemia Cell Lysates for Quenching ATP Metabolism ~500,000 K562 cells were used per sample. The cells were washed with PBS prior to adding 50 µL of the cell lysis buffer (10, 25, 35, or 50% BMIM acetate in water (w/v)) or control solution (PBS or DI water). Cells were incubated with the lysis or control solution for 5, 30, 60, or 240 min. After incubation, cell samples were either centrifuged at 4° C. or put on ice. After the supernatant was removed from the centrifuged samples, all samples were flash frozen on dry ice and stored at −80° C. overnight.

The following day, samples were thawed, and aliquots were taken for the ATP assay using the One Solution CellTiter Glo reagent from Promega. ATP standard curves were made using 0.001-1 µM ATP, with a separate standard curve for each lysis solution or control solution used to treat the cells.

Results of the ATP analysis are reported in FIG. 4. BMIM acetate was found to slightly decrease the bioluminescent light output of the CellTiter Glo reagent, so standard curves were made with ATP and each concentration of BMIM acetate tested to determine the ATP concentration in the cell samples. 50% BMIM acetate was found to maintain ATP levels extracted from cells over four hours at room temperature, while ATP degradation was found in all other samples over the same time period. Furthermore, the 50% BMIM acetate solutions have the highest ATP levels, suggesting this level of BMIM acetate is able to extract more ATP from the cells than any other condition.

Example 4. Analysis of Peak Areas for Metabolite Standards in the Presence or Absence of Ammonium Acetate The impact of ammonium acetate on the LCMS analysis of metabolite standards was assessed with two different concentrations of ammonium acetate, 210 mM (see FIG. 5A) and 420 mM (see FIG. 5B). For many metabolite standards, the peak areas are either equivalent to or greater than the peak areas without any added ammonium acetate.

A few metabolite standards show decreased peak areas in the presence of ammonium acetate, notably glucose, trehalose, reduced glutathione, and acetoacetyl CoA. Glucose and trehalose both have early elution times in these runs, thus they may be eluting from the column when there is a higher content of ammonium acetate eluting from the column. Thus, glucose and trehalose may have reduced signal due to ion suppression from the ammonium acetate or glucose and trehalose may be forming adducts with the ammonium acetate that were not included in this analysis. Notably, although most metabolite standards maintain their peak area when 420 mM ammonium acetate is added to the sample, some of the peak shapes are not ideal with 420 mM ammonium acetate and peak fronting and/or peak doubling is seen. With 210 mM ammonium acetate and a 3 or 4 µl injection volume, the peak shapes of the metabolite standards are consistent with samples without ammonium acetate.

Example 5. Comparative Analysis of Metabolomics Samples Comprising Ammonium Acetate FIG. 6 provides spectra for metabolomic samples prepared by a traditional metabolomic sample preparation method as compared to the ionic workflow which forms potassium chloride. See the upper panel in FIG. 6.

FIG. 6 also provides spectra for metabolomic samples prepared by a traditional metabolomic sample preparation method as compared to the ionic workflow which forms ammonium acetate. See the lower panel in FIG. 6.

Plots of relative peak areas of compound features detected in cell samples prepared using either a traditional metabolomic sample preparation method or the ionic liquid workflow that forms either potassium chloride or ammonium acetate. Color intensity of the plots indicates the relative peak area for each compound feature found. Profinder was used to identify peaks and integrate peak areas using Batch Recursive Feature Extraction. The minimum threshold for peak height was set to 10,000 counts.

Addition of potassium chloride to samples prepared using a traditional metabolomics sample preparation method reduces the number of compound features that can be detected. See the upper panel in FIG. 6.

The ionic liquid method that forms potassium chloride forms a sample that has the same loss of compound features seen with potassium chloride addition to the traditional method sample. The ionic liquid method that forms potassium chloride has other metabolite features that are missing in addition to the compound features that are decreased with potassium chloride addition. See the upper panel in FIG. 6.

Addition of ammonium acetate to samples prepared using a traditional method has limited impact on the compound features detected and their peak areas. The ionic liquid method that forms ammonium acetate makes a sample with compound features that are comparable to those found with the traditional method. Additionally, when using the ammonium acetate forming ionic liquid method, there are a number of compound features found that are not found using the traditional sample preparation method. These compound features may be additional metabolites that are extracted from cells that are not extracted using the traditional method or they may be non-metabolite compounds added to the sample during steps in the ionic liquid method. See the lower panel in FIG. 6.

What is claimed is:

1. A method for preparing an aqueous solution comprising metabolites and a mass spectrometry-compatible volatile salt or volatile compound, the method comprising:
    mixing a solution comprising metabolites and an ionic liquid, wherein the ionic liquid comprises a positively charged organic ion and an anion that can form a volatile salt or volatile compound, with a fluorous compound comprising a cation that can form a volatile salt or volatile compound, optionally in the presence of a fluorous solvent and/or other water-immiscible solvent or liquid, and thereby obtaining a two-layer mixture in which a first layer is not miscible with a second layer, the second layer is an aqueous solution comprising metabolites and the volatile salt or volatile compound and the first layer is a water-immiscible phase comprising the positively charged organic ion of the ionic liquid; and
    collecting the aqueous solution comprising metabolites and the volatile salt or volatile compound.

2. The method of claim 1, wherein the anion comprises one or more of the following: sulfate, bisulfate, carbonate, bicarbonate, acetate anion, formate anion, trifluoroacetate anion, a conjugate base of an organic acid with 1 to 15 carbons, sulfide, hydrogen sulfide, cyanide, dicyanamide, nitrate, trichloroacetate anion, hydroxide, hydride, borate, a heteroatom derivative, an alkene derivative, an alkyne derivative of an organic acid with 1 to 15 carbons, or any combination thereof.

3. The method of claim 1, wherein the cation comprises one or more of the following: ammonium, trimethyl ammonium, pyridinium ion, imidazolium ion, piperidinium ion, pyrimidine conjugate acid, hydrogen cation (hydron), hydronium, triethylammonium, diethylammonium, morpholinium, 4-methylmorpholinium, 1-methylpiperidinium, pyrrolidinium, a nitrogen-containing conjugate acid of a weak base, or any combination thereof.

4. The method of claim 1, wherein the volatile salt or volatile compound comprises:
   one or more of the following anions: sulfate, bisulfate, carbonate, bicarbonate, acetate anion, formate anion, trifluoroacetate anion, a conjugate base of an organic acid with 1 to 15 carbons, sulfide, hydrogen sulfide, cyanide, dicyanamide, nitrate, trichloroacetate anion, hydroxide, hydride, borate, or any combination thereof; and/or
   one or more of the following cations: ammonium, trimethyl ammonium, pyridinium ion, imidazolium ion, piperidinium ion, pyrimidine conjugate acid, hydrogen cation (hydron), hydronium, triethylammonium, diethylammonium, morpholinium, 4-methylmorpholinium, 1-methylpiperidinium, pyrrolidinium, a nitrogen-containing conjugate acid of a weak base, or any combination thereof.

5. The method of claim 1, wherein the method is conducted in the presence of the water-immiscible solvent or liquid and wherein the liquid is one or more of the following: hexane/hexanes, tetrahydrofuran, dichloromethane, chloroform, butane, cyclohexane, heptane/heptanes or any combination thereof.

6. The method of claim 1, wherein the volatile salt or volatile compound comprises one or more of the following compounds: formic acid, acetic acid, trifluoroacetic acid, ammonium formate, ammonium acetate, ammonium hydroxide, water, triethylamine acetate, triethylamine formate, diethylamine acetate, diethylamine formate, piperidine acetate, piperidine formate, ammonium bicarbonate, borate, hydride, 4-methylmorpholine, 1-methylpiperidine, pyrrolidine acetate, pyrrolidine formate, or any combination thereof.

7. The method of claim 1, wherein the positively charged organic ion in the ionic liquid is defined by one of the following formulas (I) through (VI):

(I)

where each of $R^1$ and $R^2$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl;

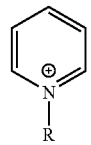
(II)

where R is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl;

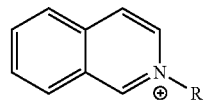
(III)

where R is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl;

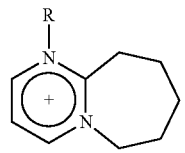
(IV)

where R is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl;

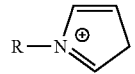
(V)

where R is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl;

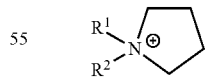
(VI)

where each of $R^1$ and $R^2$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl.

8. The method of claim 1, wherein the ionic liquid comprises 1-hexyl-3-methyl-imidazolium (HMIM) acetate, 1-butyl-3-methyl-imidazolium (BMIM) acetate, HMIM formate, and/or BMIM formate.

9. The method of claim 1, wherein the method is conducted with one or more of the fluorous compounds with the following general formula (VII):

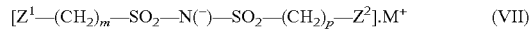
$$[Z^1—(CH_2)_m—SO_2—N(^-)—SO_2—(CH_2)_p—Z^2].M^+ \quad (VII)$$

wherein: $M^+$ is the cation that can form a volatile salt or volatile compound and $Z^1$ and $Z^2$ are independently a perfluoroalkyl, an alkyl, a substituted alkyl, a perfluoroaryl, an aryl, or a substituted aryl, wherein $Z^1$ and $Z^2$ include together a combined total of 8 or more fluorinated (e.g., perfluorinated) carbon atoms (e.g., 9 or more, 10 or more, 11 or more, 12 or more, 13 or more, 14 or more, 15 or more, 16 or more, 17 or more, 18 or more, 19 or more, 20 or more, 30 or more or 40 or more fluorinated carbon atoms); and m and p are independently 0, 1 or 2.

10. The method of claim 1, wherein the fluorous compound comprising the cation is bis((perfluorohexyl)sulfonyl)imide formulated with one or more of the following cations: ammonium, trimethyl ammonium, pyridinium ion, imidazolium ion, piperidinium ion, pyrimidine conjugate acid, hydrogen cation (hydron), hydronium, triethylammonium, diethylammonium, morpholinium, 4-methylmorpholinium, 1-methylpiperidinium, pyrrolidinium or a nitrogen-containing conjugate acid of a weak base.

11. The method of claim 1, wherein the fluorous solvent comprises a perfluorocarbon (PFC), a hydrofluoroether (HFE), perfluorohexane, perfluoromethylcyclohexane, perfluorodecalin, nanofluorobutyl methyl ether, or any combination thereof.

12. The method of claim 1, wherein the method further comprises at least one of the following steps:
lysing a biological sample; and/or
quantifying metabolites in the aqueous solution comprising metabolites and the volatile salt or volatile compound by direct injection mass spectrometry, liquid chromatography/mass spectrometry, gas chromatography/mass spectrometry, ion mobility/mass spectrometry, supercritical fluid chromatography/mass spectrometry, or any combination thereof.

13. The method of any one of claim 1, wherein the ionic liquid and/or the solution comprising metabolites further comprises one or more of water-miscible solvents.

14. The method of claim 1, wherein the ionic liquid and/or the solution comprising metabolites further comprises acetonitrile, methanol, ethanol, acetone, dimethylformamide, dimethylsulfoxide or any mixture thereof.

15. A method for manual or automatable ionic liquid workflow, the method comprising:
1) contacting a biological sample with one or more ionic liquids comprising one or more anions, thereby obtaining a mixture comprising metabolites and the ionic liquid(s);
2) performing a metathesis reaction, wherein the one or more anions of the ionic liquid reacts with a cation of a fluorous compound and produces a metabolite solution comprising a volatile salt or volatile compound; and
3) separating a water-immiscible phase from an aqueous phase, the aqueous phase comprising the metabolite solution.

16. The method of claim 15, wherein the method further comprises removing fluorine-containing contaminants from the metabolite solution.

17. The method of claim 15, wherein the biological sample comprises cells and the step of contacting the biologic sample with the one or more ionic liquids lyses the cells.

18. The method of claim 15, wherein the method further comprises separating cell and/or other debris comprising enzymes, proteins, DNA, RNA and/or lipids from the mixture comprising metabolites and the ionic liquid.

19. A kit for obtaining a metabolite solution, the kit comprising one or more ionic liquids that comprises one or more anions that can form one or more volatile salts or volatile compounds and a fluorous compound comprising one or more cations that can form one or more volatile salts or volatile compounds; and wherein the kit further comprises one or more of the following: a phase separator material or column; a debris removal filtering device or column, a cell culture device that comprises a filter, a fluorous affinity column, a fluorous solvent, a water-immiscible solvent or liquid, a water-miscible solvent, a water-miscible solvent that is mixed with water, or any combination thereof.

20. The kit of claim 19, wherein one or more from: the phase separator material or column; the debris removal filtering device or column; the cell culture device that comprises a filter; and/or the fluorous affinity column are in a multi-well format; and wherein the multi-well format is optionally a 96-well plate, a 48-well plate, a 24-well plate, a 12-well plate, or a 6-well plate.

* * * * *